United States Patent [19]

Zondler et al.

[11] 4,436,892
[45] Mar. 13, 1984

[54] IMIDAZOLIDES

[75] Inventors: Helmut Zondler, Bottmingen; Friedrich Lohse, Oberwil; Roland Moser, Basel, all of Switzerland

[73] Assignee: Ciba-Geigy Corporation, Ardsley, N.Y.

[21] Appl. No.: 447,344

[22] Filed: Dec. 6, 1982

[30] Foreign Application Priority Data

Dec. 15, 1981 [CH] Switzerland ............. 7992/81

[51] Int. Cl.³ ............. C08G 59/54; C08G 59/44
[52] U.S. Cl. ............. 528/117; 525/504; 528/94; 528/361; 528/365; 548/341
[58] Field of Search ............. 525/504; 528/94, 117, 528/361, 365; 548/341

[56] References Cited

U.S. PATENT DOCUMENTS 3,394,105  7/1968  Christie ............. 528/94
3,634,323  1/1972  Moran ............. 528/94

FOREIGN PATENT DOCUMENTS 49-743212 of 1974 Japan .

Primary Examiner—Earl A. Nielsen
Attorney, Agent, or Firm—Harry Falber

[57] ABSTRACT

Novel imidazolides (N-acylimidazoles) of the formula I wherein
$R_1$ is hydrogen, $C_1$–$C_{12}$-alkyl or phenyl, and $R_2$ is hydrogen, or
$R_1$ is ethyl, and $R_2$ is methyl, or
$R_1$ is hydrogen, and $R_2$ is phenyl or methyl, and
$R_3$ is a group of any one of the formulae II–VI wherein $X_1$ is hydrogen, chlorine or $NO_2$, and $X_2$ is hydrogen or $NO_2$.

The imidazolides are suitable as curing agents for polyepoxide compounds.

10 Claims, No Drawings

IMIDAZOLIDES

The present invention relates to novel imidazolides (N-acylimidazoles), to a process for producing them, and to their use as curing agents for polyepoxide compounds having on average more than one epoxide group in the molecule.

The use of imidazolides as curing agents for the curing of epoxide resins is known. Imidazolides, for example 1-(2-chlorobenzoyl)-imidazole, are thus described as effective curing agents in the Japanese Patent Specification No. 743 212. Mixtures of polyepoxides with these imidazolides can be stored for some time at room temperature with the exclusion of water, and can then be cured at elevated temperature by the absorption of water vapour from the atmosphere.

There is however a need for highly reactive curing agents which are stable to atmospheric moisture, and which therefore permit of longer storage and processing times. It has now been found that the novel imidazolides satisfy these requirements.

The present invention hence relates to imidazolides of the formula I $$R_3-\overset{O}{\underset{\|}{C}}-N\underset{\underset{R_1}{Y}}{\overset{\phantom{X}}{\phantom{X}}}N-R_2 \quad (I)$$

wherein
$R_1$ is hydrogen, $C_1$–$C_{12}$-alkyl or phenyl, and $R_2$ is hydrogen, or
$R_1$ is ethyl, and $R_2$ is methyl, or
$R_1$ is hydrogen, and $R_2$ is phenyl or methyl, and
$R_3$ is a group of any one of the formulae II-VI (II), (III), (IV), (V), (VI)

wherein $X_1$ is hydrogen, chlorine or $NO_2$, and $X_2$ is hydrogen or $NO_2$.

When $R_1$ in the formula I is $C_1$–$C_{12}$-alkyl, it can be for example: methyl, ethyl, isopropyl, n-butyl, tert-butyl, n-hexyl, 2-ethylhexyl or n-dodecyl.

Preferred imidazolides of the formula I are those wherein $R_1$ is phenyl, and $R_2$ is hydrogen.

Also preferred are imidazolides of the formula I wherein $R_3$ is a group of the formula II, and particularly preferred are those wherein $X_1$ in the formula II is hydrogen.

More especially preferred is the compound: 1-(2,6-dichlorobenzoyl)-2-phenylimidazole.

The imidazolides of the formula I according to the invention are obtained by reacting an acid halide of the formula VII $$R_3-\overset{O}{\underset{\|}{C}}-X_3, \quad (VII)$$

in the presence of an acid acceptor, with an imidazole of the formula VIII $$HN\underset{\underset{R_1}{Y}}{\phantom{X}}N-R_2 \quad (VIII)$$

wherein $X_3$ is chlorine or bromine, and the symbols $R_1$, $R_2$ and $R_3$ have the meanings defined in the foregoing.

The substances customarily used for the purpose are suitable as acid acceptors, for example tertiary amines, especially triethylamine, and pyridine bases, or the imidazole of the formula VIII in a molar excess.

The reaction is advantageously performed in an inert organic solvent. Suitable solvents are for example: aromatic hydrocarbons, such as toluene or xylene; halogenated aliphatic or aromatic hydrocarbons, for example $CCl_4$, $HCCl_3$, $CH_2Cl_2$, ethylene chloride or chlorobenzene, dichlorobenzene or chloronaphthalene; and ethers, such as diethyl ether, diisopropylether, dioxane or tetrahydrofuran.

The reaction is advantageously performed in the temperature range of 0° to 150° C.

The acid halides and imidazoles used as starting compounds are obtainable commercially, or can be produced by known methods.

The imidazolides according to the invention are excellently suitable as curing agents for epoxide resins. Further subject matter of the present invention is formed therefore by curable mixtures which contain an imidazolide of the formula I, together with a polyepoxide compound having on average more than one epoxide group in the molecule.

The mixture ratio can be selected so that the curable mixtures contain 0.005 to 0.5 mol, preferably 0.01 to 0.2 mol, of imidazolide of the formula I per epoxide equivalent.

Polyepoxide compounds suitable for the curable mixtures according to the invention are those having on average more than one glycidyl group of β-methylglycidyl group bound to a hetero atom, preferably oxygen or nitrogen, or such compounds having on average more than one epoxycyclohexyl grouping. The following may for example be mentioned:

(a) di- or polyglycidyl ethers of polyhydric, aliphatic alcohols, such as 1,4-butanediol or neopentyl glycol, or of polyalkylene glycols, such as polypropylene glycols;

(b) di- or polyglycidyl ethers of cycloaliphatic polyols, such as 2,2-bis-(4-hydroxycyclohexyl)-propane and 1,4-bis-(hydroxymethyl)-cyclohexane;

(c) di- or polyglycidyl ethers of polyhydric phenols, such as resorcin, bis-(p-hydroxyphenyl)-methane, 2,2-bis-(p-hydroxyphenyl)-propane (=diomethane), 2,2- bis-(4'-hydroxy-3',5'-dibromophenyl)-propane, 1,1,2,2-tetrakis-(p-hydroxyphenyl)-ethane, or condensation products of phenols with formaldehyde, obtained under acid conditions, such as phenol-novolaks and cresol-novolaks;

(d) di- or poly-($\beta$-methylglycidyl)-ethers of the aforementioned polyhydric alcohols or polyhydric phenols;

(e) compounds having epoxycyclohexyl groupings, such as 3,4-epoxycyclohexylcarboxylic acid-3',4'-epoxycyclohexylmethyl ester, 3-(3',4'-epoxycyclohexyl)-2,4-dioxa-spiro-[5,5]-8,9-epoxyundecane or adipic acid-bis-(3,4-epoxycyclohexylmethyl)-ester;

(f) di- or polyglycidyl esters of polyvalent carboxylic acids, such as phthalic acid, terephthalic acid, $\Delta^4$-tetrahydrophthalic acid, hexahydrophthalic acid, trimellitic acid, oxalic acid, malonic acid, adipic acid, succinic acid, fumaric acid or maleic acid; and (g) N-glycidyl derivatives of amines, amides and heterocyclic nitrogen bases, such as N,N-diglycidylaniline, N,N-diglycidyltoluidine, N,N,N',N'-tetraglycidyl-bis-(p-aminophenyl)-methane, triglycidyl compounds of p-hydroxyaniline, triglycidylisocyanurate, N,N'-diglycidylethyleneurea, N,N'-diglycidyl-5,5-dimethylhydantoin, N,N'-diglycidyl-5-isopropylhydantoin and N,N'-diglycidyl-5,5-dimethyl-6-isopropyl-5,6-dihydrouracil.

It is also possible to use mixtures of the stated di- and polyepoxides.

The curing of the curable mixtures according to the invention to produce shaped objects and such like is advantageously performed in the temperature range of 20°–250° C., preferably between 50° and 180° C. Curing can be effected in the known manner also in two or more stages, the first curing stage being carried out at low temperature and the subsequent curing at a higher temperature.

If the gelling or curing times are to be shortened, known curing catalysts can be used. Suitable catalysts are for example: tertiary amines, such as triethylamine or benzyldimethylamine, pyridine and substituted pyridine derivatives, such as dimethylaminopyridine or N-p-chlorophenyl-N,N'-dimethylurea ("Monuron"). The catalysts can be used in amounts of 0.1 to 5% by weight, preferably 0.1 to 2% by weight, relative to the reaction mixture.

There can be added to the curable mixtures according to the invention, in some phase before curing, also customary modifying agents, such as extenders, fillers and reinforcing agents, pigments, dyes, organic solvents, plasticisers, levelling agents, thixotropic agents, fire-retarding substances or internal mould lubricants.

Extenders, reinforcing agents, fillers and pigments which can be used in the curable mixtures according to the invention are for example: bituminous coal tar, bitumen, liquid coumarone-indene resins, textile fibres, glass fibres, asbestos fibres, boron fibres, carbon fibres, cellulose, polyethylene powder, polypropylene powder, quartz powder, mineral silicates, such as mica, asbestos powder, powdered slate, kaolin, aluminium oxide trihydrate, powdered chalk, gypsum, antimony trioxide, bentone, silicic acid aerogel, lithopone, heavy spar, titanium dioxide, carbon black, graphite, oxide pigments, such as iron oxide, or metal powders, such as aluminium powder or iron powder.

Organic solvents suitable for modification of the curable mixtures are for example: toluene, xylene, butyl acetate, acetone and methyl ethyl ketone.

Plasticisers which can be used for modifying the curable mixtures are for example: dibutyl-, dioctyl- and dinonylphthalate, tricresyl phosphate, triphenyl phosphate and diphenoxyethyl formal.

Levelling agents which can be added with application of the curable mixtures in particular for surface protection are for example: silicones, liquid acrylic resins, cellulose acetate butyrate, polyvinyl butyral, waxes, stearate, and so forth, (which are employed in part also as internal mould lubricants).

The curable mixtures according to the invention can be produced, in the customary manner, with the use of known mixing apparatus (stirrers, kneaders, rollers or, in the case of solid substances or powders, in mills or dry mixers). A brief heating of the mixture is necessary in some cases in order to obtain sufficient homogeneity.

The imidazolides of the formula I used in the mixtures according to the invention are latent, highly reactive curing agents. They are particularly suitable for producing storage-stable single-component systems.

The curable mixtures according to the invention are used in particular in the field of surface protection, in the electrical industry, in the lamination process, in the adhesives industry and in the building trade. They can be applied as a formulation adapted to suit the specific purpose of application, in the unfilled or filled condition, optionally in the form of solutions or emulsions, as coating compounds, solvent-free coatings, sinter powders, moulding compounds, injection-moulding formulations, dipping resins, casting resins, impregnating resins, foam plastics, films, sheets, matrix materials, binders and adhesives, tool resins, laminating resins, sealing compounds and stopping materials, flooring materials, and binders for mineral aggregates.

PRODUCTION EXAMPLES

EXAMPLE 1

1-(2,6-Dichlorobenzoyl)-2-methyl-imidazole

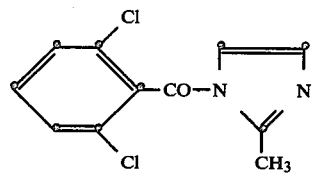

20.5 g of 2-methylimidazole and 25.3 g of triethylamine are dissolved in 200 ml of tetrahydrofuran. To this solution are added dropwise, within 15 minutes at reflux temperature, 52.4 g of 2,6-dichlorobenzoyl chloride (dissolved in 100 ml of tetrahydrofuran). The mixture is refluxed for 30 minutes, and subsequently freed from triethylamine hydrochloride by filtration in vacuo. The filtrate is concentrated to dryness in a rotary evaporator and the residue is recrystallised from 130 ml of acetonitrile. The crystals are filtered off with suction, washed with acetonitrile, and dried at 60° C. in vacuo to thus obtain 46.0 g (72.2% of theory) of the product, m.p. 116°–119° C.

Analysis: $C_{11}H_8N_2Cl_2O$; molecular weight: 225.10. Calculated: C 51.79%; H 3.16%; N 10.98%. Found: C 51.75%; H 3.18%; N 11.25%.

Concentration of the mother liquor by evaporation yields a further 8.2 g of the desired product (12.9% of theory); m.p. 112°–114° C. The recrystallised pure substance melts at 119°–121° C.

EXAMPLE 2

1-(2,6-Dichlorobenzoyl)-2-phenyl-imidazole

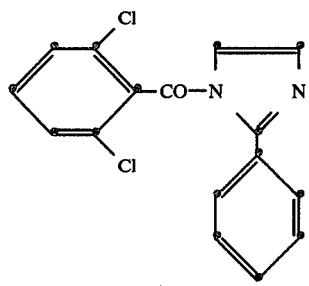

173 g of 2-phenylimidazole are dissolved in 600 ml of tetrahydrofuran. To this solution are added dropwise at boiling temperature 129.4 g of 2,6-dichlorobenzoyl chloride, dissolved in 400 ml of tetrahydrofuran, and the mixture is refluxed for 1 hour. The phenylimidazole hydrochloride which precipitates is separated at room temperature by vacuum filtration. The solvent of the filtrate is subsequently removed in the rotary evaporator, and the residue is recrystallised from 600 ml of acetonitrile. The yield after filtration with suction, washing with acetonitrile and drying is 153 g (80.4% of theory) of the product, m.p. 116°–117° C. There are obtained by concentrating the mother liquor by evaporation a further 22.3 g (11.7% of theory) of the product, m.p. 110°–114° C. For the analysis, 3.0 g of the compound are recrystallised from 5 ml of acetonitrile, washed with acetonitrile and dried at 60° C. in vacuo; yield: 2.6 g, m.p. 117°–118° C.

Analysis: $C_{16}H_{10}Cl_2N_2O$; molecular weight: 317.18. Calculated: C 60.59%; H 3.18%; N 8.83%. Found: C 60.61%; H 3.33%; N 8.88%.

The mass spectrum shows the two molecular peaks caused by $^{35}Cl$ and $^{37}Cl$ at m/e 316 and 318.

EXAMPLE 3

1-(2,6-Dichlorobenzoyl)-2-ethyl-4-methylimidazole

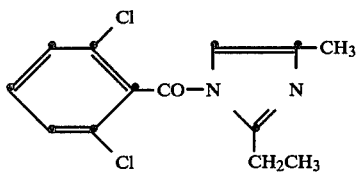

22.02 g of 2-ethyl-4-methyl-imidazole and 20.85 g of triethylamine are dissolved in 250 ml of tetrahydrofuran. There are then added dropwise, at reflux temperature within 20 minutes, 41.88 g of 2,6-dichlorobenzoyl chloride, dissolved in 100 ml of tetrahydrofuran, and the mixture is refluxed for 30 minutes, and subsequently further processed as described in Example 1. Recrystallisation of the crude product from 120 ml of acetonitrile yields 36.4 g of product (64.3% of theory), m.p. 112°–113.5° C.

Analysis: $C_{13}H_{12}N_2Cl_2O$; molecular weight: 283.16. Calculated: C 55.14%; H 4.27%; N 9.89%. Found: C 55.13%; H 4.31%; N 10.09%.

Concentration of the mother liquor by evaporation yields a further 7.5 g (13.3% of theory) of the desired product, m.p. 111.5°–113° C.

EXAMPLE 4

1-(2,6-Dichlorobenzoyl)-4-phenyl-imidazole

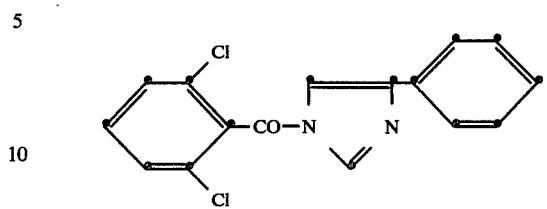

2.88 g of 4-phenylimidazole are dissolved in 7 ml of tetrahydrofuran; a solution of 2.12 g of dichlorobenzoyl chloride in 5 ml of tetrahydrofuran is then added, and the mixture is heated, in the course of which 4-phenylimidazole hydrochloride precipitates. The mixture is diluted with 15 ml of tetrahydrofuran, and is filtered at room temperature in vacuo. The filtrate is subsequently evaporated to dryness in a rotary evaporator, and the residue is recrystallised from 15 ml of ethyl acetate. The yield is 1.55 g (48.9% of theory) of the desired product, m.p. 135°–136° C. By concentration of the mother liquor by evaporation and recrystallisation from 8 ml of benzene, there are obtained a further two fractions (0.76 g, m.p. 135°–136° C.; and 0.41 g, m.p. 134°–135° C.). The total yield is hence 2.72 g (85.8% of theory).

Analysis: $C_{16}H_{10}Cl_2N_2O$; molecular weight: 317.18. Calculated: C 60.59%; H 3.18%; N 8.83%. Found: C 60.48%; H 3.37%; N 8.81%.

EXAMPLE 5

1-(2-Chloro-6-nitrobenzoyl)-2-phenyl-imidazole

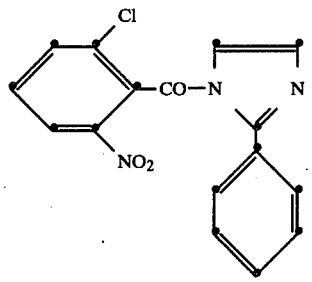

13.4 g of 2-phenylimidazole are dissolved in 120 ml of tetrahydrofuran; 9.7 g of triethylamine are added, and there are then added dropwise, at reflux temperature within 10 minutes, 20.5 g of 2-chloro-6-nitro-benzoyl chloride, dissolved in 40 ml of tetrahydrofuran. The mixture is refluxed for 1 hour, and the precipitated triethylamine hydrochloride is removed at room temperature by filtration in vacuo. After removal of the solvent in the rotary evaporator, the crude product is recrystallised from 65 ml of acetonitrile. The yield is 25.1 g (82.4% of theory) of product, m.p. 147°–148° C. Concentration of the mother liquor by evaporation produces a further 2.1 g (6.9% of theory) of this product, m.p. 144°–147° C.

Analysis: $C_{16}H_{10}N_3Cl\ O_3$; molecular weight: 327.73. Calculated: C 58.64%; H 3.08%; N 12.82%; Cl 10.82%. Found: C 58.76%; H 3.25%; N 12.98%; Cl 10.85%.

EXAMPLE 6

1-(2-Chloro-6-nitrobenzoyl)-2-ethyl-4-methylimidazole

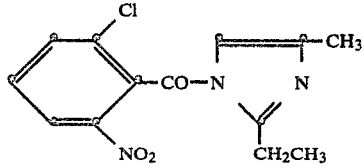

15.4 g of 2-ethyl-4-methyl-imidazole are dissolved in 100 ml of tetrahydrofuran; 14.6 g of triethylamine are added, and there can then added dropwise, within 30 minutes at reflux temperature, 30.8 g of 2-chloro-6-nitrobenzoyl chloride, dissolved in 50 ml of tetrahydrofuran, in the process of which triethylamine hydrochloride precipitates. After 3 hours of refluxing, the mixture is filtered with suction, and the solvent is removed in the rotary evaporator. Recrystallisation of the residue from 85 ml of toluene yields 27.7 g (67.3% of theory) of the desired product, m.p. 119°–120° C.

Analysis: $C_{13}H_{12}N_3Cl\ O_3$; molecular weight: 293.71. Calculated: C 53.16%; H 4.12%; N 14.31%; Cl 12.07%. Found: C 53.24%; H 4.15%; N 14.16%; Cl 12.14%.

By concentration of the mother liquor by evaporation, there are obtained a further 7.0 g (17.1% of theory) of final product, m.p. 116°–118° C.

EXAMPLE 7

1-Pentachlorobenzoyl-2-methyl-imidazole

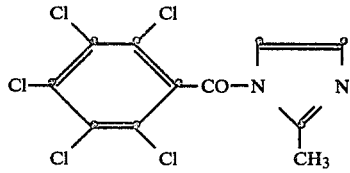

1.89 g of 2-methylimidazole, 7.20 g of pentachlorobenzoyl chloride and 2.40 g of triethylamine are refluxed in 50 ml of tetrahydrofuran for 1 hour. The formed triethylamine hydrochloride is removed by filtration in vacuo, and the filtrate is subsequently evaporated to dryness in the rotary evaporator. Recrystallisation of the residue from 32 ml of acetonitrile yields 5.23 g (64.5% of theory) of the desired product, m.p. 137°–141° C. A further 0.63 g of the product, m.p. 128°–142° C. is obtained by concentrating the mother liquor by evaporation. For the analysis, the product is recrystallised afresh from acetonitrile, and is dried at 60° C. in vacuo, m.p. 142°–143° C.

Analysis: $C_{11}H_5Cl_5N_2O$; molecular weight: 358.44. Calculated: C 36.86%; H 1.41%; N 7.82%. Found: C 36.63%; H 1.50%; N 7.82%.

EXAMPLE 8

1-Pentachlorobenzoyl-2-phenyl-imidazole

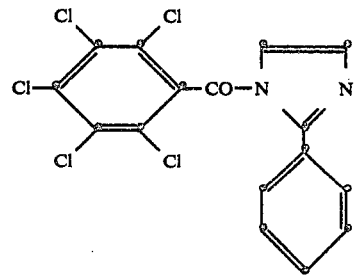

A solution of 20.2 g of 2-phenylimidazole and 14.6 g of triethylamine in 200 ml of tetrahydrofuran is heated to reflux. To this solution are added dropwise, within 30 minutes, 43.7 g of pentachlorobenzoyl chloride, dissolved in 100 ml of tetrahydrofuran, and the mixture is refluxed for 45 minutes. The formed triethylamine hydrochloride is subsequently removed by filtration in vacuo at room temperature, and the filtrate is evaporated to dryness in the rotary evaporator. Recrystallisation of the residue from 500 ml of acetonitrile yields 51.2 g (87.0% of theory) of the desired product, m.p. 158°–159° C.

Analysis: $C_{16}H_7Cl_5N_2O$; molecular weight: 420.51. Calculated C 45.70%; H 1.68%; N 6.66%. Found: C 45.99%; H 1.84%; N 6.71%.

EXAMPLE 9

1-Pentachlorobenzoyl-2-ethyl-4-methyl-imidazole

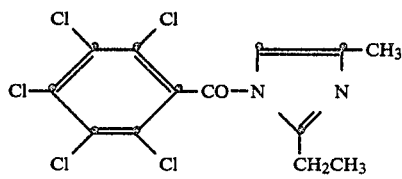

2.2 g of 2-ethyl-4-methyl-imidazole and 6.25 g of pentachlorobenzoyl chloride together with 2.08 g of triethylamine in 65 ml of tetrahydrofuran are refluxed for 30 minutes. The formed triethylamine hydrochloride is subsequently removed by filtration in vacuo, and the filtrate is concentrated to dryness by evaporation in the rotary evaporator. Recrystallisation of the residue from 35 ml of acetonitrile yields 4.77 g (61.7% of theory) of product, m.p. 136.5°–138° C. A further 1.01 g of final product, m.p. 137°–138° C., are obtained by concentrating the mother liquor by evaporation. For the analysis, a specimen is again recrystallised from acetonitrile, m.p. 138°–139° C.

Analysis: $C_{13}H_9Cl_5N_2O$; molecular weight: 386.49. Calculated: C 40.40%; H 2,35%; N 7.25%. Found: C 40.25%; H 2.51%; N 7.37%.

APPLICATION EXAMPLES 10–18

Viscosity measurement

From one of the imidazolides described in the Examples 1 to 9 and a polyepoxy compound (bisphenol-A-diglycidyl ether; epoxide content: 5.33 val/kg), there is prepared a specimen, the amounts used of the components being such that in each case there is 1 mol of an imidazolide to 10 equivalents of epoxide. The mixture is slightly warmed until there is formed a solution having optimum homogeneity. A few drops of this solution are then placed into a viscosimeter (Epprect rotational viscosimeter) preheated to 80° C., and the changes in viscosity of the solution are measured as a function of time. The results are summarised in the Table which follows.

TABLE

| Application Example | Imidazolide | Initial viscosity (mPa.s) | Time until attainment of twice the initial viscosity | 1000 mPa.s |
|---|---|---|---|---|
| 10 | 2,6-dichlorobenzoyl-N-(isopropenyl)imidazolide (CH₃) | 60 | 2 hrs. 35 min. | 3 hrs. 30 min. |
| 11 | 2,6-dichlorobenzoyl-N-(α-styryl)imidazolide | 73 | 4 hrs. 30 min. | 5 hrs. 28 min. |
| 12 | 2,6-dichlorobenzoyl-N-(1-ethylpropenyl)-4-methylimidazolide | 60 | 13 hrs. 30 min. | 17 hrs. |
| 13 | 2,6-dichlorobenzoyl-N-(α-styryl)-4-phenylimidazolide | 78 | 18 hrs. | 22 hrs. 20 min. |
| 14 | pentachlorobenzoyl-N-(isopropenyl)imidazolide | 85 | 4 hrs. 40 min | 7 hrs. 15 min. |
| 15 | pentachlorobenzoyl-N-(α-styryl)imidazolide | 82 | 7 hrs. 10 min. | 10 hrs. |
| 16 | pentachlorobenzyl-N-(1-ethylpropenyl)-4-methylimidazolide | 75 | 24 hrs. | >40 hrs. |

TABLE-continued

| Application Example | Imidazolide | Initial viscosity (mPa.s) | Time until attainment of twice the initial viscosity | 1000 mPa.s |
|---|---|---|---|---|
| 17 | (structure: 2-chloro-6-nitrobenzoyl-2-phenylimidazole) | 87 | 3 hrs. 37 min. | 4 hrs. 30 min. |
| 18 | (structure: 2-chloro-6-nitrobenzoyl-2-ethyl-4-methylimidazole) | 78 | 6 hrs. 15 min. | 7 hrs. 45 min. |

What is claimed is:

1. An imidazolide of the formula I $$R_3-\overset{O}{\underset{\|}{C}}-N\underset{\underset{R_1}{Y}}{\overset{\frown}{\phantom{N}}}N-R_2 \qquad (I)$$

wherein
$R_1$ is hydrogen, $C_1$-$C_{12}$-alkyl or phenyl, and $R_2$ is hydrogen, or
$R_1$ is ethyl, and $R_2$ is methyl, or
$R_1$ is hydrogen, and $R_2$ is phenyl or methyl, and
$R_3$ is a group of any one of the formulae II–VI (II) 2,3,6-trichlorophenyl with $X_1$; (III) pentachlorophenyl; (IV) 2-chloro-6-nitrophenyl with $X_2$; (V) 2,4-dinitrophenyl; (VI) 2,4,6-tribromophenyl wherein $X_1$ is hydrogen, chlorine or $NO_2$, and $X_2$ is hydrogen or $NO_2$.

2. An imidazolide according to claim 1, wherein $R_1$ is phenyl, and $R_2$ is hydrogen.

3. An imidazolide according to claim 1, wherein $R_3$ is a group of the formula II.

4. An imidazolide according to claim 3, wherein $X_1$ in the group of the formula II is hydrogen.

5. An imidazolide according to claim 1, which is 1-(2,6-dichlorobenzoyl)-2-phenylimidazole.

6. An imidazolide according to claim 1, which is 1-(2,6-dichlorobenzoyl)-2-ethyl-4-methyl-imidazole.

7. A process for producing an imidazolide according to claim 1, which process comprises reacting an acid halide of the formula VII $$R_3-\overset{O}{\underset{\|}{C}}-X_3, \qquad (VII)$$

in the presence of an acid acceptor, with an imidazole of the formula VIII $$HN\underset{\underset{R_1}{Y}}{\overset{\frown}{\phantom{N}}}N-R_2, \qquad (VIII)$$

wherein $X_3$ is chlorine or bromine, and the symbols $R_1$, $R_2$ and $R_3$ have the meanings defined in claim 1.

8. A curable mixture containing an imidazolide of the formula I according to claim 1, which mixture contains also a polyepoxide compound having on average more than one epoxide group in the molecule.

9. A curable mixture according to claim 8, which contains, as polyepoxide compound, an epoxide compound based on bisphenol-A.

10. The product obtained by curing with application of the mixture according to claim 8.

* * * * *